(12) United States Patent
Fadhel et al.

(10) Patent No.: US 10,845,293 B2
(45) Date of Patent: Nov. 24, 2020

(54) SYSTEM, APPARATUS, AND METHOD FOR DETERMINING CHARACTERISTICS OF ROCK SAMPLES

(71) Applicant: KING FAHD UNIVERSITY OF PETROLEUM AND MINERALS, Dhahran (SA)

(72) Inventors: Rakan Fadhel, Dhahran (SA); Salaheldin Elkatatny, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 175 days.

(21) Appl. No.: 16/202,760

(22) Filed: Nov. 28, 2018

(65) Prior Publication Data

US 2019/0162644 A1  May 30, 2019

Related U.S. Application Data

(60) Provisional application No. 62/591,319, filed on Nov. 28, 2017.

(51) Int. Cl.
*G01N 15/08* (2006.01)
*G01N 33/24* (2006.01)

(52) U.S. Cl.
CPC ....... *G01N 15/088* (2013.01); *G01N 15/0806* (2013.01); *G01N 33/241* (2013.01)

(58) Field of Classification Search
CPC ... G01N 15/08; G01N 15/0806; G01N 33/241
See application file for complete search history.

(56) References Cited

U.S. PATENT DOCUMENTS

| 5,587,929 | A | * | 12/1996 | League | G01S 13/931 342/159 |
| 9,507,047 | B1 | * | 11/2016 | Dvorkin | G01N 23/046 |
| 2008/0216559 | A1 | * | 9/2008 | Hilab | G01N 15/0826 73/38 |
| 2009/0260415 | A1 | * | 10/2009 | Suarez-Rivera | G01N 33/241 73/7 |
| 2010/0269578 | A1 | * | 10/2010 | Detournay | G01N 33/24 73/152.11 |
| 2011/0187375 | A1 | * | 8/2011 | Capaccioli | G01N 27/041 324/376 |

(Continued)

FOREIGN PATENT DOCUMENTS

FR  2 958 043 A1  9/2011

OTHER PUBLICATIONS

"Measuring the Resistivity of Soil Materials", Construction Division, TxDOT Designation: TEX-129-E, Aug. 1999, pp. 1-4.

*Primary Examiner* — Dominic E Hawkins
(74) *Attorney, Agent, or Firm* — Oblon, McClelland, Maier & Neustadt, L.L.P.

(57) ABSTRACT

The disclosed subject matter broadly involves a device and a method for determining characteristics of a rock sample. The rock sample can be provided in a sample receptacle. Length of the rock sample can be automatically determined when the rock sample is in the sample receptacle. A current can be provided through the rock sample, which, along with the determined length, can be used to determine one or more of resistance-, porosity-, and permeability-related characteristics of the rock sample.

20 Claims, 4 Drawing Sheets

(56) References Cited

U.S. PATENT DOCUMENTS

| | | | |
|---|---|---|---|
| 2015/0369949 A1* | 12/2015 | Cuevas | G01V 3/26 |
| | | | 324/338 |
| 2016/0341680 A1* | 11/2016 | Kadayam Viswanathan | |
| | | | G01N 24/081 |
| 2018/0010991 A1* | 1/2018 | Rohan, Sr. | B04B 13/00 |
| 2018/0045045 A1* | 2/2018 | Castillo | E21B 23/01 |
| 2018/0100780 A1 | 4/2018 | Lewis et al. | |
| 2018/0121579 A1* | 5/2018 | Fredrich | G06F 30/20 |

* cited by examiner

SYSTEM, APPARATUS, AND METHOD FOR DETERMINING CHARACTERISTICS OF ROCK SAMPLES

CROSS-REFERENCE TO RELATED APPLICATIONS

This application is based upon and claims the benefit of priority from U.S. provisional patent application 62/591,319, filed on Nov. 28, 2017, the entire contents of which are incorporated herein by reference.

SUMMARY

Generally, the present disclosure involves systems, apparatuses, and methods for determining one or more characteristics of a rock sample. More specifically, embodiments of the disclosed subject matter can determine resistivity, porosity, and/or permeability of rock samples collected in the field.

Embodiments of the disclosed subject matter can comprise a device configured to determine characteristics of a rock sample and methods and systems thereof. The method can comprise providing a device configured to determine the characteristics of the rock sample; providing the rock sample to the sample receptacle; and determining, using a processor or processing circuitry, the characteristics of the rock sample. The determining can include determining a length of the rock sample when the rock sample is on the platform in the sample receptacle and the platform is in the second position, determining resistance of the rock sample only when the rock sample is on the platform in the sample receptacle and the platform is in the second position based on the determined length of the rock sample and a determined cross-section of the rock sample, and determining porosity and/or permeability of the rock sample based on said determining the resistance. The device can include a sample receptacle configured to receive and hold the rock sample, a user interface having a display and configured to receive an input from the user, a first electrode configured to directly contact a top portion of the rock sample, a second electrode configured to directly contact a bottom portion of the rock sample, a lift configured to move a platform thereof vertically between a first position to a second position while the platform supports the rock sample inside the sample receptacle, and circuitry including the processor and a current source configured to output current for supply to the first electrode, the top portion of the rock sample to the bottom portion of the rock sample, and the second electrode.

In one or more embodiments, the disclosed subject matter can comprise a portable, two-hand-carriable device configured to determine characteristics of a rock sample. The device can comprise: a sample receptacle configured to receive and hold the rock sample; a user interface having a display and configured to receive an input from the user; a first electrode at a ceiling of the sample receptacle and configured to directly contact a top portion of the rock sample; a second electrode at a floor of the sample receptacle and configured to directly contact a bottom portion of the rock sample; a lift configured to move a platform thereof vertically between a first position to a second position while the platform supports the rock sample inside the sample receptacle, the platform defining a portion of the floor in the first position and having the second electrode thereon; and circuitry including a processor and a current source configured to output current for supply to the first electrode, the top portion of the rock sample to the bottom portion of the rock sample, and the second electrode. The circuitry can be configured to determine a length of the rock sample when the rock sample is on the platform in the sample receptacle and the platform is in the second position, determine a diameter of the rock sample when the rock sample is on the platform, measure resistance of the rock sample only when the rock sample is on the platform in the sample receptacle and the platform is in the second position based on the determined length of the rock sample and the determined diameter of the rock sample, and determine porosity and/or permeability of the rock sample based on the measured resistance.

Embodiments can also include methods of providing, making, and/or using devices and systems, or portions thereof, according to one or more embodiments of the disclosed subject matter. Further, methods according to one or more embodiments of the disclosed subject matter may be computer-implemented methods in whole or in part, for instance, via a non-transitory computer-readable storage medium storing computer-readable instructions that, when executed by a computer, cause the computer to perform the method.

The preceding summary is to provide an understanding of some aspects of the disclosure. As will be appreciated, other embodiments of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

BRIEF DESCRIPTION OF THE DRAWINGS

The accompanying drawings, which are incorporated in and constitute a part of the specification, illustrate one or more non-limiting embodiments and, together with the description, explain these non-limiting embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION

Figure 1:
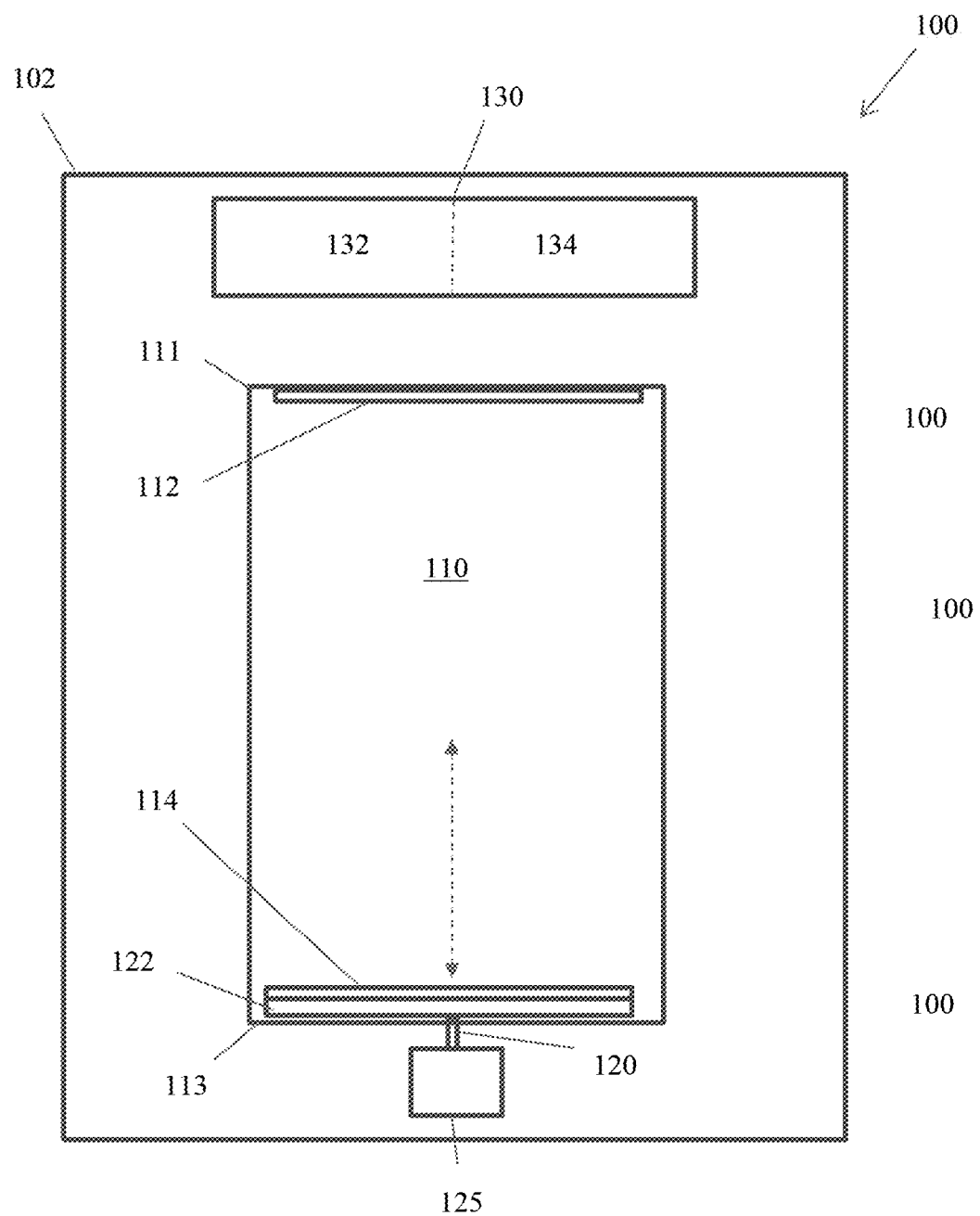
FIG. 1 is a block diagram of a device according to one or more embodiments of the disclosed subject matter.

The description set forth below in connection with the appended drawings is intended as a description of various embodiments of the described subject matter and is not necessarily intended to represent the only embodiment(s). In certain instances, the description includes specific details for the purpose of providing an understanding of the described subject matter. However, it will be apparent to those skilled in the art that embodiments may be practiced without these specific details. In some instances, structures and components may be shown in block diagram form in order to avoid obscuring the concepts of the described subject matter.

Wherever possible, the same reference numbers will be used throughout the drawings to refer to the same or the like parts.

Any reference in the specification to "one embodiment" or "an embodiment" means that a particular feature, structure, characteristic, operation, or function described in connection with an embodiment is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments.

It must also be noted that, as used in the specification, appended claims and abstract, the singular forms "a," "an," and "the" include plural referents unless the context clearly dictates otherwise. That is, unless clearly specified otherwise, as used herein the words "a" and "an" and the like carry the meaning of "one or more" or "at least one." The phrases "at least one," "one or more," "or," and "and/or" are open-ended expressions that can be both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" can mean A alone, B alone, C alone, A and B together, A and C together, B and C together, or A, B and C together. It is also to be noted that the terms "comprising," "including," and "having" can be used interchangeably.

It is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations and/or functions as described herein, and likewise do not necessarily limit embodiments of the described subject matter to any particular configuration or orientation.

Control aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "circuitry," "module" or "system." Any combination of one or more computer readable storage medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, device, or portion thereof.

As noted above, the disclosed subject matter can broadly include or is broadly directed to systems, devices, and methods for determining one or more characteristics of a rock sample, such as resistivity, porosity, and/or permeability. Such systems, devices, and methods can be operated or performed in the field and, furthermore, such devices can have their own power supply and be hand-carried by one or two individuals, for instance, to and from a worksite.

There are many properties that can be used to characterize rocks, such as porosity, density, mechanical (stress and strain), thermal, and electrical properties. Resistivity can be representative of electric properties of a rock. Generally, resistivity is the measurement of the resistance of a substance to the flow of electric current. Resistivity is equal to the electric resistance of a substance having a unit volume and it can be calculated as follows:

$$R = r \times \frac{A}{L},$$

where R is the resistivity of a sample (Ωm), r is resistance of the sample (Ω), A is the cross-section area of sample (m2), and L is the length of the sample (m).

Resistivity measurements can be important in the drilling industry (e.g., petroleum industry), as resistivity can be related to the rock saturation. A length and diameter of the core sample of rock can be obtained, and then the cross-sectional area of the core can be obtained. In one or more embodiments, the length, diameter, and cross-section area can be calculated, for instance, using circuitry (e.g., a processor) of a device according to one or more embodiments of the disclosed subject matter. Resistance (r) can be measured using a circuit that may be completed by the core sample, where:

$$r = V/I$$

V is the voltage across the circuit (including the core sample) in Volts, and I is the electric current in Amperes. Discussed in more detail below, current can be passed from a top portion of the core sample (e.g., top end surface), through the body of the core sample, to a bottom portion of the core sample (e.g., bottom end surface).

As a non-limiting example of a core sample for rock, resistivity can vary from $10^5$ Ωm for dry sandstone core down to 130 Ωm and 95 Ωm for sandstone core that is saturated with fresh water and brine, respectively. The more the material can conduct electricity the less resistivity it has, since resistivity is typically relatively high in most rock minerals, crude oils, and natural gas. Resistivity is, however, typically low in water since it has dissolved cations and anions that conduct electric currents There are many factors that can affect the resistivity of rock such as porosity and saturation. Smaller porosity can generally mean smaller area that is open to current and, hence, smaller resistivity. However, larger saturation can generally mean a longer current flow path, which can reduce resistivity.

When the resistance of brine is measured, it is higher than that of a core sample saturated with brine because the area available for the current flow is reduced since the current will only flow through the saturated pore spaces because the grains are non-conductive. In addition, electric current will travel a longer path inside the pores due to the tortuosity of the rock itself.

For formation evaluation, resistivity index and formation resistivity factor can be calculated. Resistivity index can be defined as the ratio of true resistivity to the resistivity of the same rock saturated with water. Formation resistivity factor can be the ratio of the resistivity of rock saturated with water to the resistivity of that same water. Also, formation factor can be expressed as a function of porosity, pore geometry, lithology of formation, degree of cementation, and the amount of clay in the rock itself. Resistivity index and formation factor can be calculated as follows:

$$I = \frac{R_t}{R_o} = \frac{1}{S_w^n}, \text{ where } I > 1.0$$

$$F = \frac{R_o}{R_w} = c \times \phi^{-m}$$

Regarding the two equations above, I is the resistivity index, $R_t$ is the resistivity of core saturated with both oil and water ($\Omega$m), $R_o$ is the resistivity of the core saturated with 100% water ($\Omega$m), $S_w$ is water saturation, and n is saturation exponent, F is resistivity factor, $R_w$ is the resistivity of water ($\Omega$m), and C and m, are the tortuousity and cementation factors, respectively. As an example, for clean sandstone, c=0.62, m=2.15, and n=2.0.

FIG. 1 is a block diagram of a device 100 according to one or more embodiments of the disclosed subject matter. Generally, the device 100 can be configured to determine one or more characteristics of a rock sample. For example, the device 100 can determine resistivity, porosity, and/or permeability of rock. The device 100 can also determine length and/or circumference or cross-sectional area of the rock sample. The device 100 can be relatively small (e.g., 12" height and 8" width) and light-weight, for instance, such that the device 100 can be hand-carried by one or two individuals, for instance, to and from a worksite. The device 100 can operate when pressure has exceeded atmospheric pressure and/or at temperatures above or below room temperature (e.g., field temperatures). Further, rock samples can have diameters between 1.0"-1.5" or greater, such as 5.0", and lengths up to 3" or up to 10", for instance.

The device 100 can include a housing 102, a sample receptacle 110, a lift 120, a first electrode 112, and a second electrode 114. The device 100 may also have a user interface 130. Discussed in more detail below, the device 100 can also have circuitry 200 and a power source 250. Optionally, the power source 250 may be considered part of the circuitry 200, particularly in a case where the power source 250 is a self-contained power source for the device 100, such as one or more batteries.

The sample receptacle 110 can be configured to receive a rock sample. For example, the sample receptacle 110 can be sized to receive a rock sample of predetermined maximum dimensions (e.g., length and circumference). The rock sample may be saturated, for instance, with water and/or oil. In one or more embodiments of the disclosed subject matter, the sample receptacle 110 may be in the form of a cup, for instance, with a closed bottom and side(s) and an open top. Optionally, sample receptacle 110 may be created using 3-D printing techniques.

The sample receptacle 110 can hold the rock sample to determine one or more characteristics of the rock sample. For example, the sample receptacle 110 can hold the rock sample on a platform 122 of the lift 120. Thus, at least the platform 122 of the lift 120 may be inside the sample receptacle 110.

The lift 120 may move vertically between a first position and a second position, as illustrated diagrammatically in FIG. 1. FIG. 1 shows an example of the lift 120 with a platform 122 in a first position. That is, the first position of the lift 120 may be a bottom-most position where the platform 122 is not extended in the vertical direction. Optionally, the platform may define a portion of a floor 113 when in the first position.

The platform 122 may support a rock sample thereon while moving between the first and second positions. The second position may not reach a ceiling 111 of the sample receptacle 110. Further, the second position may be at a positioned determined based on the length (i.e., height) of the rock sample. For example, the platform 122 may move with the rock sample thereon from the first position to a position where the rock sample contacts a top portion of the sample receptacle, such as the ceiling 111, or the first electrode 112. Contact of the rock sample with the top portion of the sample receptacle 110 may be sensed using a sensor (e.g., an optical sensor or a mechanical stress sensor), and the lift 120 may stop raising the platform 122. The stop position of the platform 122 may be the second position. Of course, depending upon the length of the rock sample, the second position may change from sample to sample. Optionally, the rock sample may not be insertable into the sample receptacle 110 when the platform 122 is in the second position. That is, optionally, the platform 122 may be in a stow position in the second position, to prevent premature insertion of the rock sample, into the sample receptacle 110. To insert the rock sample into the sample receptacle 110, it may be necessary to lower the platform 122 to the first position, for instance, at the floor 113 of the sample receptacle 110.

Movement of the platform 122 to stop at the second position, when carrying a rock sample, may be used to determine a length of the rock sample. For example, a sensor (e.g., a linear movement sensor) may sense how far vertically the platform 122 has moved. Additionally or alternatively, a number of revolutions in a particular direction of an electric motor 125 of the lift 120 may be monitored to determine how far the platform 122 traveled and, hence, the length of the rock sample. That is, knowing a total height of the sample receptacle 110, circuitry 200 can subtract from the total height the amount of vertical movement of the platform 122 to determine the length of the rock sample. Of course, the thickness of the platform 122 and any intervening components, such as second electrode 114, may be accounted for to determine the length of the rock sample.

As shown in FIG. 1, the first electrode 112 may be at a ceiling 111 of the sample receptacle 110. The first electrode 112 can be configured to directly contact a top portion of the rock sample, such as a top end surface of the rock sample. Optionally, the first electrode 112 may be sized to cover an entire area of the top portion of the rock sample. Such configuration can provide for better contact between the first electrode 112 and the top portion of the rock sample.

The second electrode 114 may be at a bottom portion of the sample receptacle 110. For example, the second electrode 114 may be at a floor 113 of the sample receptacle 110. Further, in one or more embodiments, the second electrode 114 may be provided on an upper surface of the platform 122 of the lift 120. The second electrode 114 can be configured to directly contact a bottom portion of the rock sample, such as a bottom end surface of the rock sample.

Each of the first electrode 112 and the second electrode 114 may include a pad. Such pads may enhance the contact between the first electrode 112 and the top portion of the rock sample and the second electrode 114 and the bottom portion of the rock sample.

Alternatively, instead of a lift 120, embodiments of the disclosed subject matter may have reverse lift, meaning that the rock sample rests on the floor 113 of the sample receptacle 110 (and the second electrode 114) and the reverse lift moves a platform (and first electrode 112) downward to contact the top portion of the rock sample.

Of course, horizontal movement of lifts and reverse lifts (and corresponding electrodes) can also be implemented according to one or more embodiments of the disclosed subject matter.

According to embodiments of the disclosed subject matter, the device 100 can determine a circumference of the rock sample, in a case where the rock sample is cylindrical or generally cylindrical. Alternatively, the rock sample may be a rectangular 3-dimensional shape and, as such, the device 100 may determine a cross-sectional area of the rock sample.

The user interface 130 can include a display 132 to display results of the one or more determined characteristics of the rock sample. Optionally, the user interface 130 can include a user input 134 configured to receive one or more inputs from the user, such as characteristics of the rock sample for the device 100 to determine and/or one or more input characteristics of the rock sample, such as a circumference of the rock sample.

Figure 2:
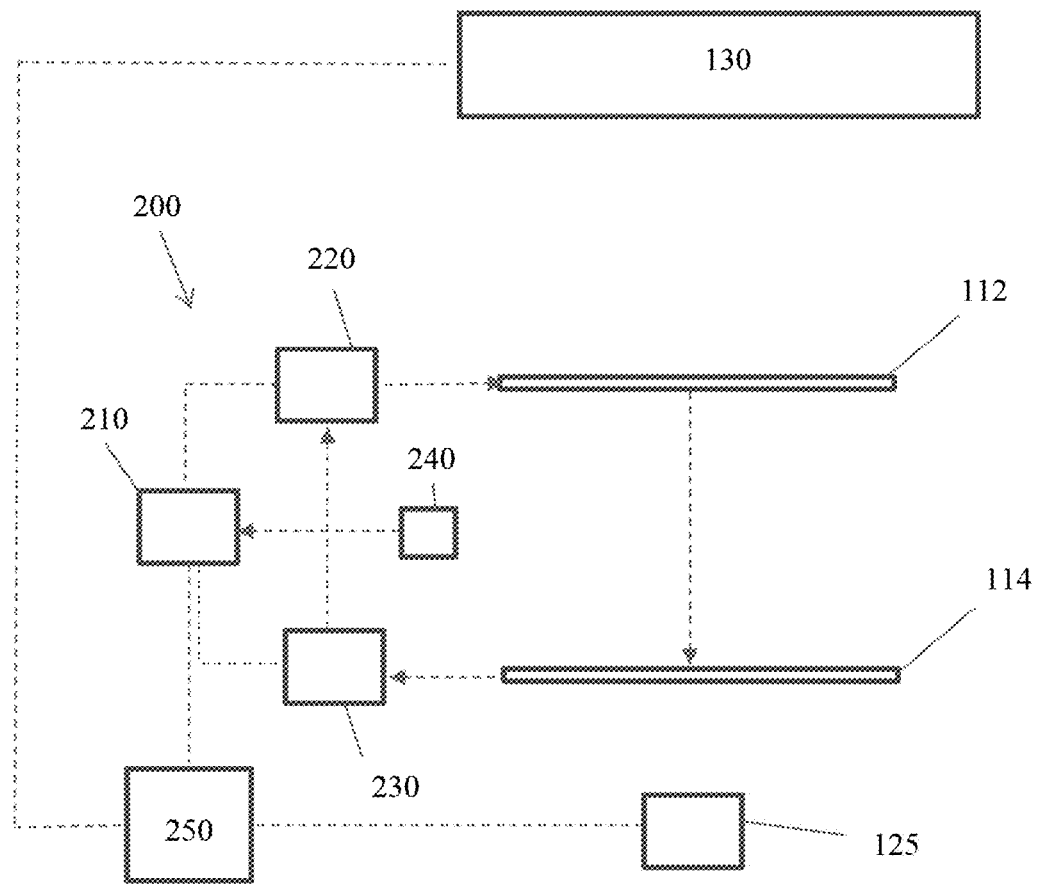
FIG. 2 is a block diagram of circuitry according to one or more embodiments of the disclosed subject matter.

Referring to FIG. 2, this figure is a block diagram of circuitry 200 according to one or more embodiments of the disclosed subject matter. FIG. 2 also shows a power source or supply 250. The power source 250 may be a self-contained power source for the device 100, such as one or more batteries. Alternatively, the power source 250 may be mains. Optionally, embodiments of the disclosed subject matter can provide a power source 250 in the form of one or more batteries and mains. Optionally, the mains power source may be used to recharge the one or more batteries.

The power source 250 may supply power to the circuitry 200 and the electrical motor 125 of the lift 120. The power source 250 can also provide power to the user interface 130. Optionally, in one or more embodiments of the disclosed subject matter, the user interface 130, or a portion thereof, may be considered part of the circuitry 200.

The circuitry 200 can include a processor 210, a current source 220, and memory (not shown). The memory may be part of the processor 210 and/or a component separate from the processor 210. The memory may store a program to operate the processor to perform methods according to embodiments of the disclosed subject matter, such as shown and described relative to FIG. 4. The memory may also store determined rock sample characteristic data, for instance, for later retrieval. The circuitry 200 may also include an ohmmeter 230 or otherwise a circuit configured to measure resistance. Optionally, the current source 220 and the ohmmeter 230 may be implemented in the processor 210.

The circuitry 200 may also include one or more sensors 240 configured to determine various characteristics of a rock sample in the sample receptacle 110. Such one or more sensors 240 may send their respective signals to the processor 210 to determine the characteristics of the rock sample. For example, a sensor, such as an optical sensor, may be used to identify a circumference or cross-sectional area of the rock sample. Optionally, such sensor may send signals, such as image capture signals, to the processor 210 to determine the circumference or cross-sectional area of the rock sample. As another example, a sensor may identify, or send signals to the processor 210 to identify, a length of the rock sample based on movement of the lift 120 to the second position.

The current source 220, which can be controlled by the processor 210, can output a current for supply to the first electrode 112 and the second electrode 114 via a rock sample properly installed in the sample receptacle 110 in direct contact with the first and second electrodes 112, 114. In general, the current, or the corresponding voltage signal, should be relatively low such that the current or voltage does not adversely affect water molecules in the rock sample.

Optionally, the current source 220 is an ammeter. The ohmmeter 230, which can be controlled by the processor 210, can measure the resistance of the rock sample based on the current provided by the current source 220.

The circuitry 200, particularly the processor 210, can determine the length of the rock sample when the rock sample is on the platform 122 in the sample receptacle 110 and the platform 122 is in the second position. As noted above, the processor 210 can receive signals from one or more sensors 240 to determine the length of the rock sample. The processor 210 can also determine a diameter, circumference or cross-sectional area of the rock sample when the rock sample is on the platform 122. The processor 210 can receive signals from one or more sensors 240 to determine the diameter, circumference or cross-sectional area of the rock sample. Alternatively, a user may manually enter the diameter, circumference or cross-sectional area manually using the user input 134 of the user interface 130.

The circuitry 200, particularly the ohmmeter 230 and the processor 210, can measure resistance of the rock sample when the rock sample is on the platform 122 and the platform is in the second position. Optionally, the ohmmeter 230 may only measure resistance when the rock sample is on the platform in the sample receptacle and the platform is in the second position. Such resistance determination can be made using the determined length of the rock sample and the determined diameter, circumference or cross-sectional area of the rock sample. The processor 210 may also determine a resistivity factor of the rock sample based on the determined resistance of the rock sample. The resistance and resistivity factor calculations can be performed using the formulas discussed above.

The circuitry 200, particularly the processor 210, can determine porosity and/or permeability of the rock sample based on the determined resistance and/or the determined resistivity factor. Optionally, both porosity and permeability of the rock sample may be determined.

The circuitry 200 can automatically determine the characteristics of the rock sample. For example, once the rock sample is properly installed in the sample receptacle 110 and the power supply 125 is supplying power (e.g., the device 100 is turned on), a user may merely press a button on the user input 134 to start the measurement operations of the device 100. The device 100 may make the relevant determinations in sequence, ultimately to determine one or more of resistance-, porosity-, and permeability-related characteristics of the rock sample.

Figure 3:
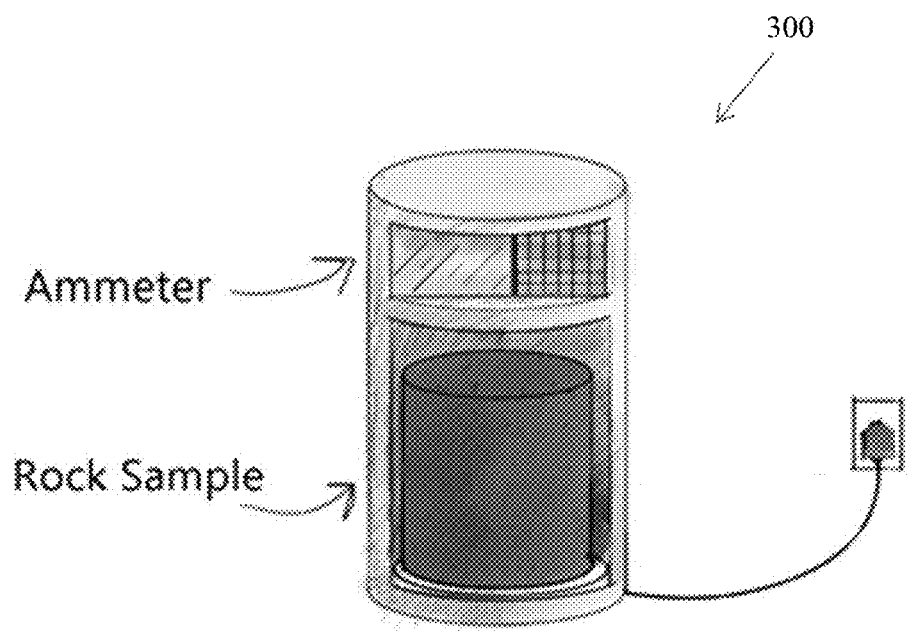
FIG. 3 an example of a device according to one or more embodiments of the disclosed subject matter.

FIG. 3 an example of a device 300 according to one or more embodiments of the disclosed subject matter. Generally, the device 300 can operate similar to device 100 discussed above with respect to FIG. 1 and FIG. 2. The device 300, however, expressly shows the rock sample and the device 300 connected to mains as the power supply. Of course, as noted above, the device 300 may also have one or more batteries as the power supply. Optionally, mains may be used to recharge the batteries.

The device 300 can have an automated length reader built in, where once the rock sample is provided inside the device

300 the platform will rise to a certain point (i.e., second position) and stop to make the measurement for the length and the other parameters.

Generally, the voltage source (or current source) provided to the rock sample is generally low to prevent or minimize any adverse impact to the water molecules. For example, the voltage may be from 3-5 volts. Rock sample characteristic readings calculated by the device 300 can be displayed on the display screen. Further, optionally, there are two fixed points on the top of the device 300 and at the bottom (i.e., top and bottom of the sample receptacle), and the processor of the device 300 can calculate the resistance through the core sample, and, optionally, the value can be stored in memory. Based on the determined resistance, the device 300 can calculate porosity, saturation, and formation resistivity factor. As non-limiting examples, circuitry of the device 300 can include a breadboard, jumper wires, an ohmmeter, and a current source (e.g., an ammeter).

Figure 4:
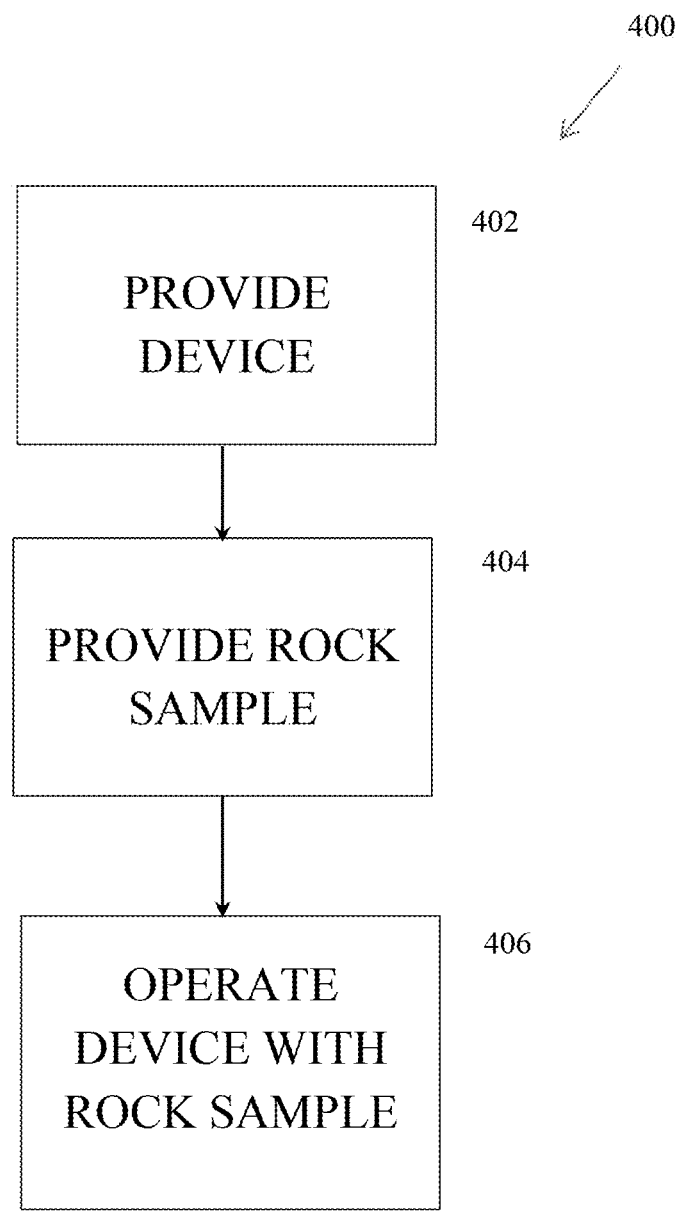
FIG. 4 is a flow chart of a method according to one or more embodiments of the disclosed subject matter.

FIG. 4 is a flow chart of a method 400 according to one or more embodiments of the disclosed subject matter.

At 402, the method 400 can include providing a device according to one or more embodiments of the disclosed subject matter, such as device 100 or device 300 discussed above.

At 404 the method 400 can include providing a rock sample as discussed herein. The rock sample may be provided in a sample receptacle, such as described herein. Further, the rock sample can be provided in direct contact with a second electrode as described herein.

At 406, the method can include operating a device according to one or more embodiments of the disclosed subject matter, such as device 100 or device 300 discussed above.

Operation of the device can include movement of a lift such that the rock sample moves vertically from a first position to a second position. Based on movement of the lift the length of the rock sample can be determined, for instance, using circuitry described herein, such as circuitry 200. Movement vertically of the rock sample can be such that the rock sample comes into direct contact with a first electrode. As this point, the rock sample can be in direct contact with first and second electrodes. Prior to or after vertical movement of the rock sample, the circumference or cross-sectional area of the rock sample can be determined or otherwise provided. Current from a current source can be output from through the first electrode, the rock sample, and the second electrode. The resistance of the rock sample may be determined based on the formulas discussed above, including the determine length of the rock sample. Such determination may be performed electronically using the circuitry 200, for instance. Further, porosity and/or permeability of the rock sample can be determined based on the determined resistance. Optionally, both porosity and permeability may be determined.

The results of the one or more determined characteristics may be output on a display, for instance, on display 132. Further, once the characteristics have been determined, the rock sample may be moved vertically downward and removed from the sample receptacle.

Embodiments of the disclosed subject matter may also be as set forth according to the parentheticals in the following paragraphs.

(1) A portable, two-hand-carriable device configured to determine characteristics of a rock sample comprising: a sample receptacle configured to receive and hold the rock sample; a user interface having a display and configured to receive an input from the user; a first electrode at a ceiling of the sample receptacle and configured to directly contact a top portion of the rock sample; a second electrode at a floor of the sample receptacle and configured to directly contact a bottom portion of the rock sample; a lift configured to move a platform thereof vertically between a first position to a second position while the platform supports the rock sample inside the sample receptacle, the platform defining a portion of the floor in the first position and having the second electrode thereon; and circuitry including a processor and a current source configured to output current for supply to the first electrode, the top portion of the rock sample to the bottom portion of the rock sample, and the second electrode, the circuitry being configured to determine a length of the rock sample when the rock sample is on the platform in the sample receptacle and the platform is in the second position, determine a diameter of the rock sample when the rock sample is on the platform, measure resistance of the rock sample only when the rock sample is on the platform in the sample receptacle and the platform is in the second position based on the determined length of the rock sample and the determined diameter of the rock sample, and determine porosity and/or permeability of the rock sample based on the measured resistance.

(2) The device according to (1), wherein the circuitry includes an ohmmeter to measure the resistance of the rock sample.

(3) The device according to (1) or (2), wherein the rock sample is saturated with water and/or oil.

(4) The device according to any one of (1) to (3), wherein the sample receptacle is a cup.

(5) The device according to any one of (1) to (4), further comprising a power supply configured to supply power to the circuitry.

(6) The device according to any one of (1) to (5), wherein the power supply is a local power supply in the form of one or more batteries.

(7) The device according to any one of (1) to (6), wherein the current source is an ammeter.

(8) The device according to any one of (1) to (7), wherein the lift includes an electric motor to move the platform of the lift between the first and second positions.

(9) The device according to any one of (1) to (8), wherein the rock sample is not insertable into the sample receptacle when the platform is in the second position.

(10) The device according to any one of (1) to (9), wherein the circuitry is configured to determine porosity and permeability of the rock sample.

(11) The device according to any one of (1) to (10), wherein the circuitry is configured to determine a resistivity factor of the rock sample based on the determined resistance of the rock sample, and wherein the determining of the porosity and/or permeability of the rock sample uses the determined resistivity factor.

(12) A method of determining characteristics of a rock sample comprising: providing a device configured to determine the characteristics of the rock sample, the device including: a sample receptacle configured to receive and hold the rock sample, a user interface having a display and configured to receive an input from the user, a first electrode configured to directly contact a top portion of the rock sample, a second electrode configured to directly contact a bottom portion of the rock sample, a lift configured to move a platform thereof vertically between a first position to a second position while the platform supports the rock sample inside the sample receptacle, and circuitry including a processor and a current source configured to output current for supply to the first electrode, the top portion of the rock sample to the bottom portion of the rock sample, and the second electrode; providing the rock sample to the sample receptacle; and determining, using the processor, the characteristics of the rock sample, said determining the characteristics of the rock sample including: determining a length of the rock sample when the rock sample is on the platform in the sample receptacle and the platform is in the second position, determining resistance of the rock sample only when the rock sample is on the platform in the sample receptacle and the platform is in the second position based on the determined length of the rock sample and a determined cross-section of the rock sample, and determining porosity and/or permeability of the rock sample based on said determining the resistance.

(13) The method according to (12), wherein said determining porosity and/or permeability of the rock sample determines both porosity and permeability of the rock sample.

(14) The method according to (12) or (13), further comprising moving the rock sample on the platform of the lift vertically from the first position to the second position prior to said determining the characteristics of the rock sample.

(15) The method according to any one of (12) to (14), further comprising, after said determining the characteristics of the rock sample, moving the rock sample on the platform of the lift vertically from the second position to the first position.

(16) The method according to any one of (12) to (15), wherein the rock sample is saturated with water and/or oil.

(17) The method according to any one of (12) to (16), wherein the sample receptacle is a cup.

(18) The method according to any one of (12) to (17), wherein said determining the resistance of the rock sample includes providing current through the first electrode, the top portion of the rock, the bottom portion of the rock sample, and the second electrode.

(19) The method according to any one of (12) to (18), wherein the device further includes a power supply configured to supply power to the processor, the lift, and the user interface, the power supply being a local power supply, inside a housing of the device, in the form of one or more batteries, and wherein said providing the device, said providing the rock sample to the sample receptacle, and said determining the characteristics of the rock sample is performed at a field location using only the power supply and no other form of external electrical power.

(20) The method according to any one of (12) to (19), further comprising displaying, on the display of the device, one or more of the determined characteristics of the rock sample.

(21) A resistivity cup for field operations for measuring samples comprising: an arduino breadboard; an ohmmeter, a power supply providing a current source that travels through the sample from one fixed point to the end of the sample; jumper wires for connecting the breadboard, ohmmeter and power supply; wherein the arduino breadboard is connected to the ohmmeter in a way to obtain resistance measurements of the sample and to calculate the porosity/permeability of sample.

(22) The resistivity cup of (21), wherein the cup is 3D printed.

(23) The resistivity cup of (21) or (22), wherein the cup is connected to a small programmed computer to calculate resistive properties of the samples.

(24) The resistivity cup of any one of (21) to (23), further comprising a crystal screen to display measurements of samples.

(25) A method of measuring samples in field operations comprising: providing a light-weight resistivity cup; selecting a sample and placing inside resistivity cup; automatically determining core length (L) and diameter (d) of the sample; measuring resistance of the sample; calculating resistivity factor of the sample; and calculating the porosity of the sample.

Having now described embodiments of the disclosed subject matter, it should be apparent to those skilled in the art that the foregoing is merely illustrative and not limiting, having been presented by way of example only. Thus, although particular configurations have been discussed and illustrated herein, other configurations can be and are also employed. Further, numerous modifications and other embodiments (e.g., combinations, rearrangements, etc.) are enabled by the present disclosure and are contemplated as falling within the scope of the disclosed subject matter and any equivalents thereto. Features of the disclosed embodiments can be combined, rearranged, omitted, etc., within the scope of described subject matter to produce additional embodiments. Furthermore, certain features may sometimes be used to advantage without a corresponding use of other features. Accordingly, Applicant intends to embrace all such alternatives, modifications, equivalents, and variations that are within the spirit and scope of the present disclosure. Further, it is therefore to be understood that within the scope of the appended claims, the disclosure may be practiced otherwise than as specifically described herein.

The invention claimed is:

1. A portable, two-hand-carriable device configured to determine characteristics of a rock sample comprising:
   a sample receptacle configured to receive and hold the rock sample;
   a user interface having a display and configured to receive an input from the user;
   a first electrode at a ceiling of the sample receptacle and configured to directly contact a top portion of the rock sample;
   a second electrode at a floor of the sample receptacle and configured to directly contact a bottom portion of the rock sample;
   a lift configured to move a platform thereof vertically between a first position to a second position while the platform supports the rock sample inside the sample receptacle, the platform defining a portion of the floor in the first position and having the second electrode thereon; and
   circuitry including a processor and a current source configured to output current for supply to the first electrode, the top portion of the rock sample to the bottom portion of the rock sample, and the second electrode, the circuitry being configured to
   determine a length of the rock sample when the rock sample is on the platform in the sample receptacle and the platform is in the second position,
   determine a diameter of the rock sample when the rock sample is on the platform,
   measure resistance of the rock sample only when the rock sample is on the platform in the sample receptacle and the platform is in the second position based on the determined length of the rock sample and the determined diameter of the rock sample, and
   determine porosity and/or permeability of the rock sample based on the measured resistance.

2. The device according to claim 1, wherein the circuitry includes an ohmmeter to measure the resistance of the rock sample.

3. The device according to claim 1, wherein the rock sample is saturated with water and/or oil.

4. The device according to claim 1, wherein the sample receptacle is a cup.

5. The device according to claim 1, further comprising a power supply configured to supply power to the circuitry.

6. The device according to claim 1, wherein the power supply is a local power supply in the form of one or more batteries.

7. The device according to claim 1, wherein the current source is an ammeter.

8. The device according to claim 1, wherein the lift includes an electric motor to move the platform of the lift between the first and second positions.

9. The device according to claim 1, wherein the rock sample is not insertable into the sample receptacle when the platform is in the second position.

10. The device according to claim 1, wherein the circuitry is configured to determine porosity and permeability of the rock sample.

11. The device according to claim 1,
wherein the circuitry is configured to determine a resistivity factor of the rock sample based on the determined resistance of the rock sample, and
wherein the determining of the porosity and/or permeability of the rock sample uses the determined resistivity factor.

12. A method of determining characteristics of a rock sample comprising:
providing a device configured to determine the characteristics of the rock sample, the device including:
a sample receptacle configured to receive and hold the rock sample,
a user interface having a display and configured to receive an input from the user,
a first electrode configured to directly contact a top portion of the rock sample,
a second electrode configured to directly contact a bottom portion of the rock sample,
a lift configured to move a platform thereof vertically between a first position to a second position while the platform supports the rock sample inside the sample receptacle, and
circuitry including a processor and a current source configured to output current for supply to the first electrode, the top portion of the rock sample to the bottom portion of the rock sample, and the second electrode;
providing the rock sample to the sample receptacle; and
determining, using the processor, the characteristics of the rock sample, said determining the characteristics of the rock sample including:
determining a length of the rock sample when the rock sample is on the platform in the sample receptacle and the platform is in the second position,
determining resistance of the rock sample only when the rock sample is on the platform in the sample receptacle and the platform is in the second position based on the determined length of the rock sample and a determined cross-section of the rock sample, and
determining porosity and/or permeability of the rock sample based on said determining the resistance.

13. The method according to claim 12, wherein said determining porosity and/or permeability of the rock sample determines both porosity and permeability of the rock sample.

14. The method according to claim 12, further comprising moving the rock sample on the platform of the lift vertically from the first position to the second position prior to said determining the characteristics of the rock sample.

15. The method according to claim 12, further comprising, after said determining the characteristics of the rock sample, moving the rock sample on the platform of the lift vertically from the second position to the first position.

16. The method according to claim 12, wherein the rock sample is saturated with water and/or oil.

17. The method according to claim 12, wherein the sample receptacle is a cup.

18. The method according to claim 12, wherein said determining the resistance of the rock sample includes providing current through the first electrode, the top portion of the rock, the bottom portion of the rock sample, and the second electrode.

19. The method according to claim 12,
wherein the device further includes a power supply configured to supply power to the processor, the lift, and the user interface, the power supply being a local power supply, inside a housing of the device, in the form of one or more batteries, and
wherein said providing the device, said providing the rock sample to the sample receptacle, and said determining the characteristics of the rock sample is performed at a field location using only the power supply and no other form of external electrical power.

20. The method according to claim 12, further comprising displaying, on the display of the device, one or more of the determined characteristics of the rock sample.

* * * * *